United States Patent [19]

Randklev

[11] Patent Number: 4,972,969

[45] Date of Patent: Nov. 27, 1990

[54] ASSEMBLY FOR STORING MIXING AND DISPENSING PREPARATIONS SUCH AS DENTAL MATERIALS

[75] Inventor: Ronald M. Randklev, St. Paul, Minn.

[73] Assignee: Minnesota Mining and Manufacturing Company, St. Paul, Minn.

[21] Appl. No.: 506,534

[22] Filed: Apr. 5, 1990

Related U.S. Application Data

[63] Continuation of Ser. No. 246,443, Sep. 19, 1988, abandoned.

[51] Int. Cl.⁵ .............................................. B65D 35/22
[52] U.S. Cl. .......................................... 222/1; 222/94; 222/105; 222/137; 222/145; 222/183; 222/326; 206/219
[58] Field of Search .................. 222/94, 95, 135, 137, 222/145, 326, 327, 260, 183, 386, 386.5, 1, 409, 105; 206/219, 221, 222

[56] References Cited

U.S. PATENT DOCUMENTS

| | | | |
|---|---|---|---|
| 2,404,316 | 7/1946 | Sack | 206/222 |
| 2,885,104 | 5/1959 | Greenspan | 206/222 |
| 3,351,058 | 11/1967 | Webb | 222/94 X |
| 4,131,217 | 12/1978 | Sandegren | 222/326 X |
| 4,236,516 | 12/1980 | Nilson | 222/95 X |
| 4,470,505 | 9/1984 | Korwin et al. | 206/221 X |
| 4,648,532 | 3/1987 | Green | 206/222 |
| 4,790,429 | 12/1988 | Fukushima | 206/219 |

Primary Examiner—Andres Kashnikow
Assistant Examiner—Gregory L. Huson
Attorney, Agent, or Firm—Donald M. Sell; Walter N. Kirn; James D. Christoff

[57] ABSTRACT

A disposable, single chamber ampule is initially provided with a single reactive component, with additional component or components added to the ampule immediately prior to use. The ampule is placed within a capsule, and the capsule is then secured in a holding mechanism of a dental amalgamator for mixing the ingredients. The ampule has flexible wall portions and may be compressed by finger pressure or by use of a dispenser in order to expel the mixed contents directly to an application site.

26 Claims, 4 Drawing Sheets

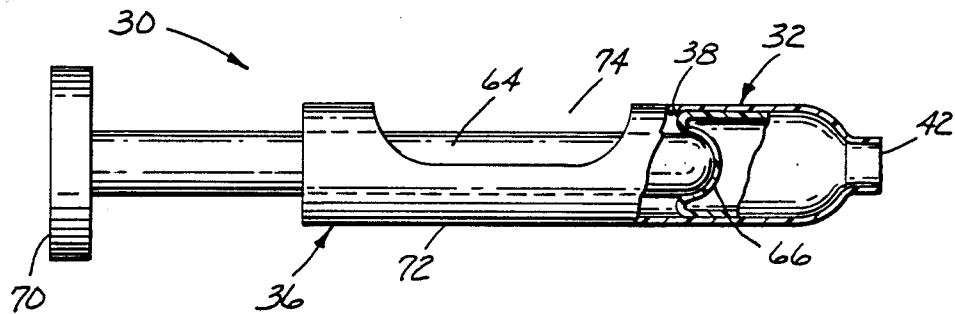
Fig. 5
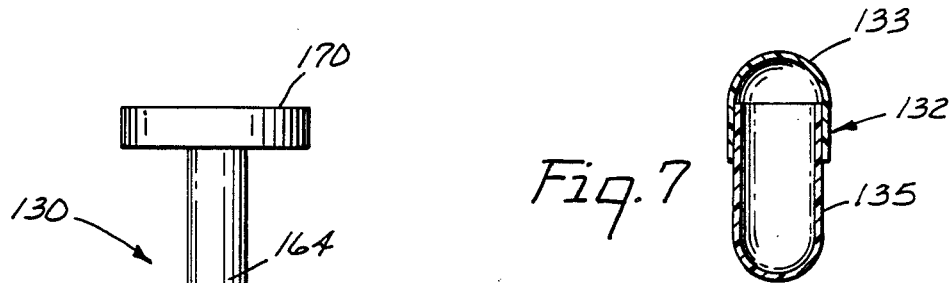
Fig. 6
Fig. 7
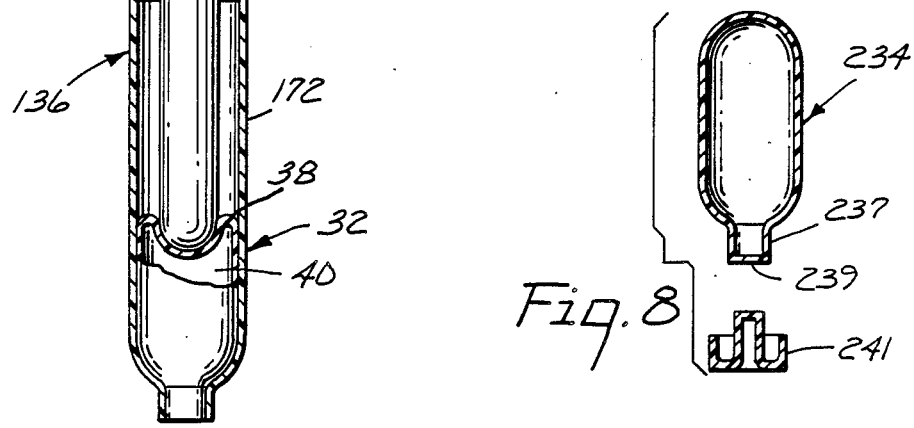
Fig. 8

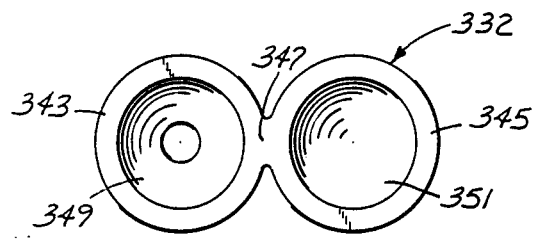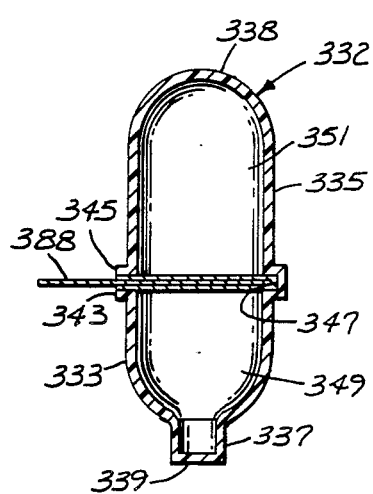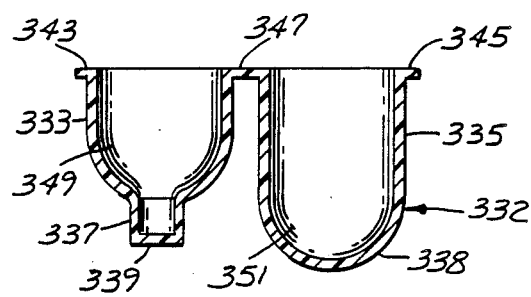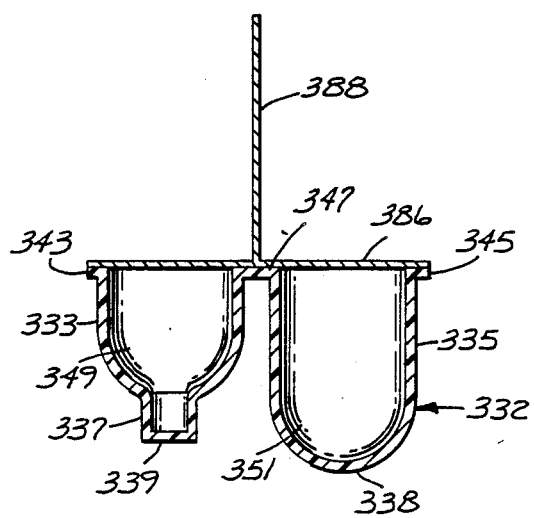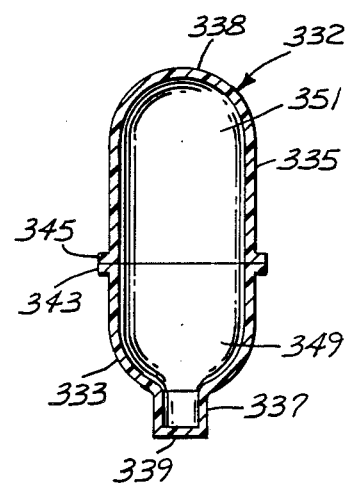

ASSEMBLY FOR STORING MIXING AND DISPENSING PREPARATIONS SUCH AS DENTAL MATERIALS

This is a continuation of application Ser. No. 07/246,443 filed Sept. 19, 1988 and now abandoned.

BACKGROUND OF THE INVENTION

1. Field of the Invention

This invention relates to a single chamber, flexible mixing ampule which is supported during a mixing operation by a complementally configured, rigid capsule.

2. Description of the Related Art

The art relating to storage and mixing of various materials is replete with devices which attempt to provide precise, convenient admixture of premeasured ingredients. Much of the art relates to storage and subsequent mixing of dental materials. For example, storage and mixing containers having a generally capsular or cylindrical configuration are described in U.S. Pat. Nos. 1,530,212, 3,543,967, 3,595,439, 3,964,643 and 4,515,267, while other storage and mixing containers with somewhat different configurations are shown, for example, in U.S. Pat. Nos. 2,874,830, 2,916,197 and 3,539,794.

A number of storage and mixing containers, including certain of the devices disclosed in the aforementioned U.S. Letters Patents, are comprised of two or more initially separate compartments that each hold one ingredient of the desired, final composition. Oftentimes, the ingredients are brought into combination with one another by rupturing a seal between the compartments, either prior to the mixing operation or as a result of a vibratory mixing motion. Such construction suffers from complexity as well as risk of premature, unintentional rupture of the seal between the compartments.

Occasionally, mixing of two or more ingredients is carried out by placing the ingredients directly into a relatively rigid capsule adapted for use with a conventional dental amalgamator. In these instances, measured quantities of each ingredient are placed within the capsule, and the capsule is then closed and placed within the amalgamator which is activated to shake the capsule and mix the ingredients. Thereafter, a spatula or other device is utilized to remove the mixed contents from the capsule for transfer to the point of use. As can be appreciated, such practice requires the dentist or dental assistant to precisely measure each ingredient, and necessitates careful cleaning and possibly sterilization of the capsule if the latter is to be re-used. Moreover, the resultant mixture in the capsule cannot be conveniently applied to the point of use without transfer to another tool or dispenser.

SUMMARY OF THE INVENTION

The present invention provides an assembly for mixing and dispensing of preparations and includes an ampule having walls defining an internal chamber for receiving a quantity of preparation, wherein the walls include an outlet opening. The assembly also includes a capsule which has means defining a- internal compartment generally complemental in configuration to the configuration of the ampule, and the compartment removably receives the ampule in substantially surrounding relation thereto. At least certain portions of the ampule walls are flexible and selectively moveable in lateral directions for expelling at least a portion of the quantity of preparation through the outlet opening.

The ampule is preferably disposable and supplied with a single, pre-dosed reactive ingredient, and additional ingredients are added just before the mixing operation. By comparison, the capsule is re-usable and has rigid walls that protect the thin walls of the ampule during the mixing operation. The ampule may be compressed to expel the mixed ingredients directly to an application site and may then be discarded, while the capsule remains clean and ready for the next mixing operation.

BRIEF DESCRIPTION OF THE DRAWINGS

FIG. 5 is a reduced, side elevational view wih parts broken away in section of a dispenser having a plunger of the type shown in FIG. 4 for infolding the ampule illustrated in FIG. 1;

FIG. 6 is a reduced, side cross-sectional view of another dispenser for infolding the ampule and ejecting the contents toward an application site;

FIG. 7 is a side cross-sectional view of a disposable ampule constructed in accordance with another embodiment of the invention;

FIG. 8 is a side cross-sectional view of a disposable ampule and cap according to another form of the invention;

FIG. 9 is a side cross-sectional view of an ampule constructed in accordance with yet another embodiment of the present invention;

FIG. 10 is a plan view of the ampule shown in FIG. 9, depicting two initially separate chamber portions for receiving different ingredients;

FIG. 11 is a side cross-sectional view similar to FIG. 9 except that a sheet-like cover has been placed over the two ampule portions for preventing spillage of the ingredients contained therein;

FIG. 12 is a side cross-sectional view of the ampule shown in FIGS. 9–11 after one of the ampule end portions has been pivoted about an 180 degrees arc to bring the two ampule portions in a general alignment with each other;

FIG. 13 is a view somewhat similar to FIG. 12 except that the cover has been removed to permit intermixing of the ingredients;

DESCRIPTION OF THE PREFERRED EMBODIMENTS

Figure 1:
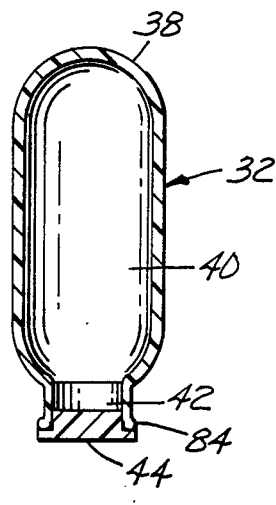
FIG. 1 is a side cross-sectional view of an ampule and stopper constructed in accordance with one embodiment of the present invention.

An apparatus 30 for storing, mixing and dispensing preparations such as dental materials is illustrated in FIGS. 1-5 and broadly includes an ampule 32, a capsule 34 and a dispenser 36. Preferably, the ampule 32 as shown in FIG. 1 is supplied with a single, pre-dosed reactive component, and additional reactive components are added just prior to mixing.

In more detail, the ampule 32 has unitary, flexible walls or wall portions 38 which have a generally oval-shaped configuration and which define an internal chamber 40. One end section of the ampule 32 tapers to a somewhat cylindrical, protruding neck which defines an outlet opening 42 that is initially closed with a friction-fit stopper 44 (FIG. 1) or other similar means. The stopper 44 is removed to add additional reactive components or ingredients to the chamber 40 by a dropper or syringe; alternately, the stopper 44 may be of a composition suitable for enabling protrusion of a syringe needle directly into the chamber 40 for addition of other reactive ingredients.

Figure 3:
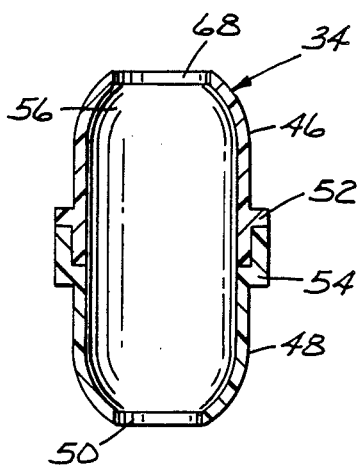
FIG. 3 is a side cross-sectional view of a capsule adapted to complementally receive the ampule shown in FIG. 1.
Figure 4:
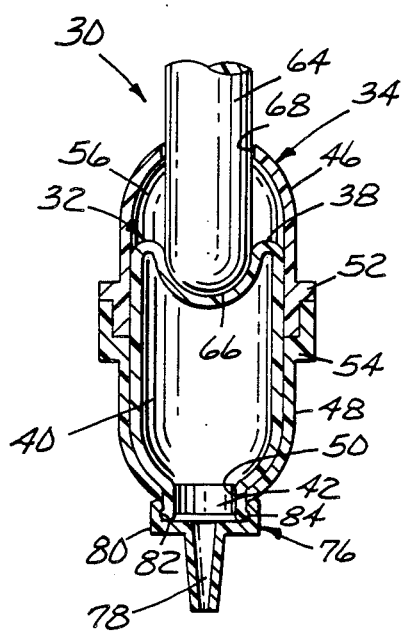
FIG. 4 is a side cross-sectional view of a capsule somewhat similar to that shown in FIG. 3 along with the ampule of FIG. 1, except that the stopper has been removed and a plunger inserted through a hole in the capsule to compress the ampule and expel the contents through an annular opening at a remote end of the ampule.
Figure 14:
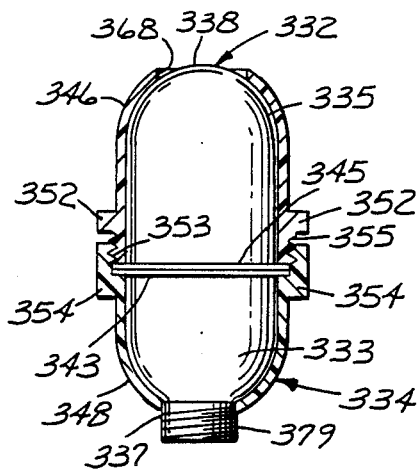
FIG. 14 is a side cross-sectional view of the ampule shown in FIG. 13 along with a surrounding capsule for use in an amalgamator.

The capsule 34 as illustrated in FIGS. 3 and 4 includes a first capsule segment 46 and a second capsule segment 48, the latter of which is formed with a circular, endmost opening 50 (FIG. 3). Each of the capsule segments 46, 48 has enlarged flanged portions 52, 54 which receive each other in sliding, telescopic relation and are held in place by a slight frictional or interference fit. Alternatively, each of the flange portions 52, 54 may be provided with mating threaded regions for interconnecting and disconnecting the capsule segments 46, 48 as desired.

As can be understood by reference to FIG. 3, the capsule 34 has two convex end portions which extend outwardly in opposite directions.

The capsule segments 46, 48 have internal structure defining a generally oval-shaped compartment 56 that is complemental in configuration to the normal external shape of the ampule 32. Once the desired components have been added to the chamber 40 of ampule 32, the flange portions 52, 54 of the capsule 34 are separated to permit reception of the ampule 32 in the manner shown in FIG. 4 such that the ampule neck defining the outlet opening 42 protrudes through the opening 50.

Next, the capsule 34 is placed within a holding mechanism of a conventional dental amalgamator, and the amalgamator is activated to reciprocate the capsule 34 and mix the contents of ampule 32. At this juncture, the capsule segments 46, 48 may be separated and the ampule 32 removed, and subsequently the mixed contents may be taken from the chamber 40 either by use of a hand-held instrument or by compressing the flexible wall portions 38 of the ampule 32 between the thumb and forefinger to expel the mixed contents.

Alternatively, the mixed ingredients may be expelled from the ampule 32 by means of a plunger 64 such as that shown in FIGS. 4 and 5. The plunger 64 has a rounded tip 66 to minimize rupture of the flexible wall portions 38 during infolding of the ampule 32. As depicted in FIG. 4, the ampule 32 may remain within the capsule 34 in order to securely support the ampule 32 during the dispensing operation. The first capsule segment 46 is formed with a circular hole 68 remote from the opening 50 in order to permit intrusion of the plunger 64 into compartment 56 for contact with the ampule 32.

Preferably, the plunger 64 forms a part of the dispenser 36 as illustrated in FIG. 5 and includes an enlarged thumb button 70 remote from the rounded tip 66. The dispenser 36 also includes a generally cylindrical main body or structure 72 with a side opening 74 for receiving the ampule 32. While the dispenser 36 as shown in FIG. 5 is constructed to receive only the ampule 32, it is to be understood in this regard that the structure 72 may alternatively be sized to receive the capsule 34 with the ampule 32 therein.

Figure 2:
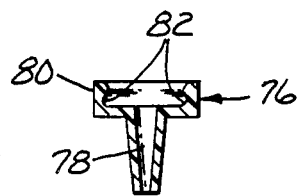
FIG. 2 is a side cross-sectional view of a delivery tube for optional use with the ampule shown in FIG. 1 after removal of the stopper therefrom.

A delivery tube 76 as illustrated in FIG. 2 is optionally placed over the neck of the ampule 32 forming the outlet opening 42 for guiding application of the mixed contents of ampule 32 directly to the desired site. The delivery tube 76 has a central, internal passageway 78 along with a cap-like region 80 that is formed with an internal, annular groove or recess 82. Once the stopper 44 is removed from the ampule 32, the delivery tube 76 is coupled to the ampule 32 in snap-fit relation and is held in place by means of an out-turned lip 84 (FIG. 4) that is formed on the outer end of the neck defining outlet opening 42.

The disposable ampule 32 of the present invention may be comprised of any one of a number of flexible materials such as polyethylene, polypropylene or a material sold under the trademark "Surlyn" and available from DuPont. Other inexpensive, flexible materials which are impermeable and unreactive with the ingredients or preparations may also be utilized. On the other hand, the capsule 34 is reuseable and is preferably constructed of somewhat more rigid materials such as acrylonitrile butadiene styrene ("ABS"), and may be machined or injection molded.

The ampule 32 is snugly received within the compartment 56 of capsule 34 to minimize damage to the thin flexible wall portions 38 during the mixing operation. In particular, the external configuration of the ampule 32 is essentially identical to the configuration of the compartment 56 and the interior of capsule 34 is in complemental engagement with essentially the entire exterior extend of the ample 32 so that the ampule 32 cannot shift in a lateral or longitudinal direction relative to the capsule 34; further, opposite end portions of the ampule 32 and the compartment 56 have complemental, generally semi-spherical shapes. If ampules 32 of varying sizes are to be employed, mating capsules 34 with varying, matching wall thicknesses may be constructed so that, in each instance, the ampule 32 is complementally received in the capsule 34 while the latter is securely held within the holding mechanism of a conventional amalgamator.

Turning now to FIG. 6, an alternative form of the invention is shown and includes a dispenser 136 which has a central body or structure 172 similar to the dispenser 36 shown in FIG. 5. A plunger 164 is shiftably coupled to the structure 172 for movement upon depression of a thumb button 170. In the dispenser 136 shown in FIG. 6, however, the plunger 164 includes a pair of annular, outwardly extending guides or spacers 165 which function to stably guide the plunger 164 such that the longitudinal axis of the latter is coincident with the longitudinal axis of an ampule-receiving barrel within the structure 172.

Each of the dispensers 36, 136 is constructed so that the plunger 64, 164 respectively contacts the central, outermost end of the ampule 32 as the plunger 64, 164 is advanced. In this manner, the flexible wall portions 38 of the ampule 32 may be infolded without damage and substantially all of the contents within the ampule chamber 40 may be expelled at the opposite end through the outlet opening 42 without waste as the plunger 64, 164 moves along a path coincident with the longitudinal axis of ampule 32.

A variation of the ampule 32 shown in FIG. 1 is illustrated in FIG. 7 and is designated by the numeral 132. In this case, the ampule 132 is comprised of two ampule sections 133, 135 which may initially hold a single-dose component. The sections 133, 135 are separated when desired to add additional reactive components, and the sections 133, 135 are then sealed with an external tape (not shown) and placed within the compartment 56 of capsule 34 for subsequent mixing by means of a dental amalgamator.

Another variation of the invention is shown in FIG. 8 and, in this instance, comprises a unitary capsule 234 that is formed with a protruding neck 237 initially closed by an integrally formed cover 239. The neck 237 is severed to remove the cover 239 when desired for the addition of other reactive components to a measured component previously placed within the ampule 232. Once the neck 237 is severed, a cap 241 is inserted within the outlet opening to prevent leakage of the contents during the mixing operation.

Other embodiments of the invention are shown in FIGS. 9–17 and include an ampule 332 having a first ampule section 333 and a second ampule section 335 as perhaps best understood by reference to FIGS. 9 and 10. The sections 333, 335 have outwardly extending, annular flanges 343, 345 which are integrally joined by a connecting hinge portion 347. Moreover, the first ampule portion 333 terminates in an outwardly extending neck 337 initially closed by an integral cover 339.

Each of the ampule portions 333, 335 thereby presents an initially separate chamber portion 349, 351 correspondingly which each hold different reactive components of the final desired preparation or composition. Once the components are in place in chamber portions 349, 351, a flexible, flat cover sheet 386 is placed in flat, face-to-face contact with the flanges 343, 345 to seal the chamber portions 349, 351 and substantially prevent spillage of the components.

Advantageously, top surfaces of the flanges 343, 345 are provided with a quantity of pressure-sensitive adhesive suitable for use with the composition of the ampule 332. The adhesive holds the cover sheet 386 in place and precludes, for all practical purposes, leakage of the contents from the chamber portions 349, 351. Optionally, an upstanding pull tab 388 may be integrally connected with the cover sheet 386 in perpendicular relationship thereto in order to provide a convenient means for removing the cover sheet 386 when desired.

To minimize spillage of the contents of the ampule 332, it is desirable to pivot the second ampule portion 335 about the hinge portion 347 and through an arc of 180 degrees until the ampule 332 is in the configuration shown in FIG. 12. At that time, and with the ampule sections 333, 335 maintained in slightly spaced relation to each other, the pull tab 388 may be grasped to remove the cover sheet 386 from flanges 343, 345 and thereby permit intermixing of the components initially placed within chamber portions 349, 351. Subsequently, the previously mentioned pressure-sensitive adhesive functions to hold the flanges 343, 345 in flat, mating, face-to-face contact with each other in the manner shown in FIG. 13 to substantially prevent accidental leakage of the contents of ampule 332.

Next, the ampule 332 is placed within a generally rigid capsule 334 (FIG. 14) that is similar to capsule 34 in essential respects but is instead provided with complemental threaded regions 353, 355 formed in flanges 352, 354 in order to facilitate coupling and uncoupling of capsule segments 346, 348. In addition, it is to be noted that the flanges 343, 345 of the ampule 332 reside between a shoulder formed in the capsule flange 354 and the end of the capsule flange 352 such that the flanges 352, 354 serve to maintain the ampule flanges 343, 345 in tight, sealed contact with each other during the subsequent mixing operation.

Figure 15:
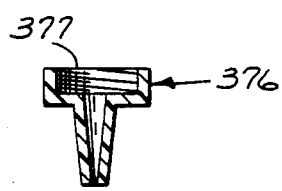
FIG. 15 is a side cross-sectional view of another delivery tube which, in this instance, may be coupled to the ampule shown in FIG. 14 for precise placement of the ampular contents to a delivery site.

A delivery tube 376 as shown in FIG. 15 is somewhat similar to the tube 76 illustrated in FIG. 2. In FIG. 15, however, the delivery tube 376 is formed with internal threads 377 which mate with external threads 379 formed on neck 337 of the ampule 332 such that the delivery tube 376 may be readily coupled to the ampule 332 when needed.

Figure 17:
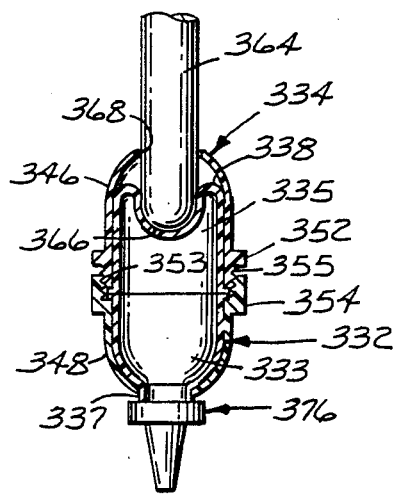
FIG. 17 is a reduced, fragmentary, side cross-sectional view of the ampule and capsule shown in FIG. 16 along with a plunger that has been lowered to infold the ampule and initiate delivery of the mixed contents.
Figure 16:
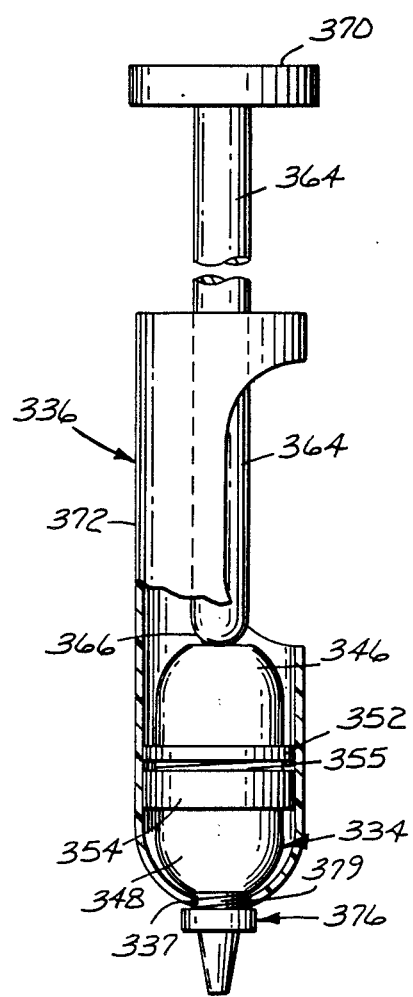
FIG. 16 is a reduced, side cross-sectional view with parts broken away in section of a dispenser along with the ampule and capsule shown in FIG. 14 for facilitating ejection of the mixed contents.

A dispenser 336 as shown in FIG. 16 is somewhat similar to the dispenser 36 illustrated in FIG. 5. However, the dispenser 336 has structure 372 with an internal barrel sized to receive the capsule 334 with the ampule 332 therein so that the latter need not be removed from the capsule 334 before the dispensing operation. As illustrated in FIG. 17, the dispenser 336 includes a plunger 364 that may be depressed by finger pressure to shift a rounded tip 366 of the plunger 364 through a hole 368 formed in the capsule 334. The rounded tip 366 is guided along a path that is coincident with the central, longitudinal axis of ampule 332 so that the flexible wall portions 338 are infolded in a direction toward the neck 337 of ampule 332, whereby substantially all the contents are expelled.

From the foregoing, it can be appreciated that the inexpensive ampule of the present invention functions as a disposable insert for the capsule so that the latter need not be cleaned after each use. Moreover, the rigid capsule serves to securely support the ampule during the mixing operation so that the flexible walls are not ruptured. Various types of compositions and preparations, ranging from liquids to viscous pastes and the like, may be prepared by means of the invention and then conveniently delivered directly to the application site at a controlled rate by the dispensers disclosed hereinabove.

We claim:

1. A method of mixing and dispensing a preparation comprising the steps of:
   providing an ampule having walls defining a chamber at least partially filled with a first component;
   opening an aperture in said walls;
   introducing a second component through said aperture and into said chamber;
   closing said aperture after said second component has been introduced into said chamber;
   placing the ampule within a complementally configured compartment of a capsule to substantially enclose the ampule;

oscillating the capsule to mix said first component with said second component within said chamber and thereby form a preparation;
establishing an outlet opening through said walls; and
flexing at least certain portions of said walls to dispense said preparation through said outlet opening,
wherein said step of establishing said outlet opening is carried out by re-opening said aperture.

2. A method of mixing and dispensing a preparation comprising the steps of:
providing an ampule having walls defining a chamber at least partially filled with a first component;
opening an aperture in said walls;
introducing a second component through said aperture and into said chamber;
closing said aperture after said second component has been introduced into said chamber;
placing the ampule within a complementally configured compartment of a capsule to substantially enclose the ampule;
oscillating the capsule to mix said first component with said second component with in said chamber and thereby form a preparation;
establishing an outlet opening through said walls; and
flexing at least certain portions of said walls to dispense said preparation through said outlet opening,
wherein said step of flexing certain wall portions includes the step of shifting a plunger through a hole formed in the capsule for contact with said wall portions.

3. A method of mixing and dispensing a preparation comprising the steps of:
providing an ampule having flexible walls defining a chamber at least partially filled with a first component;
opening an aperture in said walls;
introducing a second component through said aperture and into said chamber;
closing said aperture after said second component has been introduced into said chamber;
placing the ampule within a complementally configured compartment of a capsule comprised of two capsule sections adapted for releasable coupling to each other;
coupling the two capsule sections directly to each other in order to substantially enclose and surround the ampule;
placing the capsule with the ampule therein in a holding mechanism of a dental amalgamator;
oscillating the capsule by activating the amalgamator to mix said first component with said second component within said chamber and thereby form a preparation;
establishing an outlet opening through said walls; and
flexing to infold at least certain portions of said walls to dispense said preparation through said outlet opening.

4. The method as set forth in claim 3, wherein said step of flexing said wall portions is carried out by finger pressure.

5. The method as set forth in claim 3, wherein said step of flexing said wall portions is carried out with a plunger generally movable along a path toward said outlet opening.

6. The method as set forth in claim 3, wherein said step of opening an aperture in said wall portions includes the step of severing an initially closed neck of said ampule.

7. The method as set forth in claim 3, wherein said step of closing said aperture includes the step of placing a cap over said aperture.

8. An assembly for mixing and dispensing preparations comprising:
an ampule having walls defining an internal chamber for receiving a quantity of a preparation, said ampule having a certain external configuration including externally convex opposite end portions, at least certain portions of said walls being flexible and selectively movable in a lateral direction; and
a rigid capsule adapted to be securely held by a holding mechanism of a dental amalgamator, said capsule having a first capsule segment, a second capsule segment and means for releasably coupling said first capsule segment to said second capsule segment, said capsule having means defining an internal compartment having essentially the same configuration as the external configuration of said ampule, said compartment removably receiving said ampule in substantially surrounding relation thereto, said capsule having two externally convex end portions extending outwardly in opposite directions, said capsule end portions each having internally concave structure normally in snug, complemental engagement with said convex end portions of said ampule.

9. The assembly of claim 8, wherein said internal concave structure of said capsule end portions and said convex end portions of said ampule are rounded.

10. An assembly for mixing and dispensing preparations comprising:
an ampule having walls defining an internal chamber for receiving a quantity of a preparation, sail walls including an outlet opening; and
a capsule having means defining an internal compartment generally complemental in configuration to the configuration of said ampule, said compartment removably receiving said ampule in substantially surrounding relation thereto,
at least certain portions of said walls of said ampule being flexible and selectively movable in lateral directions for expelling at least a portion of said quantity of preparation through said outlet opening,
wherein said ampule includes a first ampule portion and a second ampule portion integrally connected to said first ampule portion for swinging, pivotal movement relative to said first ampule portion,
wherein said first ampule portion and said second ampule portion each include outwardly extending flanges disposed for contact with each other when said second ampule portion is pivoted relative to said first ampule portion.

11. The assembly of claim 10, and including a cover releasably connected to said flanges.

12. The assembly of claim 10, wherein said capsule presents a recess for reception of said flanges therein.

13. An assembly for mixing and dispensing preparations comprising:
an ampule having walls defining an internal chamber for receiving a quantity of a preparation, said walls including an outlet opening, said ampule having opposite end portions with externally convex wall sections; and
a capsule adapted to be securely held by a holding mechanism of a dental amalgamator, said capsule having two externally convex end portions extending outwardly in opposite directions, said capsule having means defining an internal compartment generally complemental in configuration to the configuration of said ampule, said compartment removably receiving said ampule in substantially surrounding relation thereto, said capsule end portions each having internally concave structure being normally in snug, complemental engagement with said convex wall sections of said ampule, at least certain portions of said walls of said ampule being flexible and selectively movable in lateral directions for expelling at least a portion of said quantity of preparation through said outlet opening.

14. The assembly of claim 13, wherein said capsule includes a hole remote from said outlet opening of said ampule for receiving a plunger moving in a path toward said ampule and generally toward said outlet opening.

15. The assembly of claim 13, wherein said ampule is formed with a outwardly protruding neck.

16. The assembly of claim 13, and including a stopper removably covering said outlet opening of said ampule.

17. The assembly of claim 13, wherein said ampule includes an outwardly extending neck defining said outlet opening; and including a delivery tube releasably coupled to said neck.

18. The assembly of claim 13, wherein said ampule includes an outwardly extending neck defining said outlet opening, and wherein said neck is integrally formed with a cover initially closing said chamber.

19. The assembly of claim 13, wherein said ampule includes a first ampule portion and a second ampule portion integrally connected to said first ampule portion for swinging, pivotal movement relative to said first ampule portion.

20. The assembly of claim 13, wherein said capsule is comprised of a first capsule segment, a second capsule segment, and means for selectively, releasably coupling said first capsule segment to said second capsule segment.

21. The assembly of claim 20, wherein said coupling means comprises mating, telescopically engageable regions.

22. The assembly of claim 20, wherein said coupling means comprises threaded regions.

23. The assembly of claim 13, wherein said ampule has a longitudinal axis; and including means for supporting said ampule; and a plunger movably coupled to said means for supporting said ampule for selective movement of said plunger in a direction generally parallel to the longitudinal axis of said ampule, said plunger being movable toward said flexible wall portions of said ampule in order to shift said wall portions in a laterally inward direction toward said chamber for expelling at least a portion of said preparation through said outlet opening.

24. The assembly of claim 23, wherein said capsule has a hole for passage of said plunger therethrough in a direction toward said flexible wall portions of said ampule.

25. The assembly of claim 23, wherein said plunger includes a rounded tip for contact with said flexible wall portions.

26. The assembly of claim 25, wherein said plunger includes an enlarged thumb button remote from said rounded tip.

* * * * *

UNITED STATES PATENT AND TRADEMARK OFFICE
CERTIFICATE OF CORRECTION

PATENT NO. : 4,972,969

DATED : November 27, 1990

INVENTOR(S) : Ronald M. Randklev and Curtis R. Nordrum

It is certified that error appears in the above-identified patent and that said Letters Patent is hereby corrected as shown below:

ON TITLE PAGE: change address of inventor Ronald M. Randklev from St. Paul, Minn. to White Bear, Minn.

add inventor Curtis R. Nordrum, St. Paul, Minn.

Col. 7, line 22, "with in" should be -- within --.

Col. 8, line 34, "sail" should be -- said --.

Signed and Sealed this

Twenty-ninth Day of September, 1992

Attest:

DOUGLAS B. COMER

*Attesting Officer*     *Acting Commissioner of Patents and Trademarks*